US006682885B1

(12) United States Patent
Kanamaru et al.

(10) Patent No.: US 6,682,885 B1
(45) Date of Patent: Jan. 27, 2004

(54) METHOD FOR DETECTING MUTATIONS USING AN URA3 REPORTER GENE

(75) Inventors: Ryunosuke Kanamaru, Sendai (JP); Chikashi Ishioka, Sendai (JP); Takao Suzuki, Sendai (JP)

(73) Assignee: SRL, Inc., Tokyo (JP)

( * ) Notice: Subject to any disclaimer, the term of this patent is extended or adjusted under 35 U.S.C. 154(b) by 0 days.

(21) Appl. No.: 09/077,734

(22) PCT Filed: Oct. 7, 1997

(86) PCT No.: PCT/JP97/03579

§ 371 (c)(1), (2), (4) Date: Jun. 9, 1998

(87) PCT Pub. No.: WO98/15654

PCT Pub. Date: Apr. 16, 1998

(30) Foreign Application Priority Data

Oct. 9, 1996 (JP) ............................................ 8/287479

(51) Int. Cl.[7] ................................................ C12G 1/68
(52) U.S. Cl. ........................................................ 435/6
(58) Field of Search ............................ 435/6; 436/501; 935/77, 78

(56) References Cited

PUBLICATIONS

Myers et al., Current Genetics, vol. 27, pp. 243–248, 1995.*
Liston et al., Journal of Virology, vol. 69, No. 11, pp. 6742–6750, 1995.*
Marwood et al., *Carcinogenesis*, vol. 16, No. 9, pp. 2037–2043 (1995).
Orita et al., *Proc. Natl. Acad. Sci. USA*, vol. 86, pp. 2766–2770 (Apr. 1989).
Alani et al., *Genetics Society of America*, vol. 117, pp. 5–12 (Sep. 1987).
Chalfie et al., *Science*, vol. 263, pp. 802–805 (Feb. 1994).
Stotz et al., *Gene*, 95, pp. 91–98 (1990).
Ammerer, *Methods in Enzymology*, vol. 101, pp. 192–201 (1983).
Miki et al., *Science*, vol. 266, pp. 66–71 (Oct. 1994).
Kinzler et al., *Science*, vol. 253, pp. 661–665 (Aug. 1991).
Sikorski et al., *Genetics*, vol. 122, pp. 19–27 (May 1989).
Ishioka et al., *Oncogene*, vol. 10, pp. 1485–1492 (1995).
FitzGerald et al., *The New England Journal of Medicine*, vol. 334, No. 3, pp. 143–149 (Jan. 1996).
Ishioka et al., *Nature Genetics*, vol. 5, pp. 124–129 (Oct. 1993).
Ito et al., *Journal of Bacteriology*, vol. 153, No. 1, pp. 163–168 (Jan. 1983).

* cited by examiner

*Primary Examiner*—Ardin H. Marschel
(74) *Attorney, Agent, or Firm*—Birch, Stewart, Kolasch & Birch, LLP

(57) ABSTRACT

A method for detecting nonsense mutations and frameshift mutations in a test nucleic acid fragment which is simple and may be used even when the size of the test nucleic acid fragment is large is disclosed. The method involves inserting the test nucleic acid fragment into a vector containing a promoter, a translational initiation codon, and a reporter gene, and transforming a host cell with the vector to express a fusion polypeptide. The production of the fusion polypeptide is assayed for in the host cell, and non-production of the fusion polypeptide is indicative of a nonsense and/or frameshift mutation in the test nucleic acid fragment.

8 Claims, 6 Drawing Sheets

METHOD FOR DETECTING MUTATIONS USING AN URA3 REPORTER GENE

This application is the national phase under 35 U.S.C. §371 of prior PCT International Application No. PCT/JP97/03579 which has an International filing date of Oct. 7, 1997 which designated the United States of America, the entire contents of which are hereby incorporated by reference.

TECHNICAL FIELD

The present invention relates to a method for detecting nonsense mutations and frameshift mutations.

BACKGROUND ART

If a structural gene has a nonsense mutation or a frameshift mutation therein, normal protein is not produced. That is, in case of a nonsense mutation, the amino acid sequence encoded by the region downstream of the mutated site is not produced at all, so that a protein shorter than the normal protein is produced. In case of a frameshift mutation, the amino acid sequence encoded by the region downstream of the mutated site is completely different from that of the normal amino acid sequence. Therefore, it is thought that, in general, existence of a nonsense mutation or a frameshift mutation in a structural gene results in a disease. Thus, it is clinically important to detect nonsense mutations and frameshift mutations in structural genes.

A method for detecting nonsense mutations or frameshift mutations in structural genes is the method for measuring the activities of the proteins encoded by the structural genes. However, measurement of protein activities often requires complicated operations and there are a number of normal proteins which do not have measurable activities. Nonsense mutations and frameshift mutations can also be detected by sequencing the entire test gene. However, this method is complicated and laborious especially when the size of the test gene is large. Mutations of DNAs can also be sensitively detected by PCR-SSCP (single-stranded conformation polymorphism). However, this method necessitates electrophoresis and it is impossible to distinguish nonsense mutations from other point mutations. Further, this method cannot be applied to large DNAs.

DISCLOSURE OF THE INVENTION

Accordingly, an object of the present invention is to provide a method for detecting nonsense mutations and frameshift mutations, which is simple, and which may be applied to large DNAs.

The present inventors intensively studied to discover that nonsense mutations and frameshift mutations may be detected by using as a reporter gene a structural gene encoding a polypeptide detectable based on a function thereof, inserting a test nucleic acid fragment into a site upstream of the reporter gene, which test nucleic acid fragment does not shift the open reading frame of the reporter gene when the test nucleic acid fragment is normal type, expressing the test nucleic acid fragment and the reporter gene downstream thereof, and by determining whether or not a fusion polypeptide having the function of the polypeptide encoded by the reporter gene is produced, thereby completing the present invention.

That is, the present invention provides a method for detecting nonsense mutations and frameshift mutations comprising the steps of inserting a test nucleic acid fragment into a site of a vector having a promoter, a translational initiation codon downstream of the promoter, a reporter gene which is a structural gene located downstream of the translational initiation codon, which is operably linked to the promoter, which encodes a polypeptide, a fusion polypeptide formed by ligating the N-terminal of the polypeptide to another polypeptide being detectable based on a function of the polypeptide encoded by the reporter gene, the site into which the test nucleic acid fragment is inserted being located downstream of the translational initiation codon and upstream of the reporter gene, the test nucleic acid fragment being one which allows, when inserted, in-frame location of the reporter gene with respect to the translational initiation codon when the test nucleic acid is normal type; expressing the test nucleic acid fragment and the reporter gene downstream thereof in the resulting recombinant vector in a host cell, and determining whether the fusion polypeptide having the function of the polypeptide encoded by the reporter gene is produced or not.

By the present invention, a method by which nonsense mutations and frameshift mutations alone may be specifically detected by simple operations was provided. By the present invention, since detection may be made without operations such as electrophoresis, the operations are very simple. Further, by using a eukaryotic cell such as yeast cell as a host, large test nucleic acid fragment up to about 3.5 kb may be examined, so that the number of fragments when a gene is divided may be reduced. Further, since mutations close to PCR-primer franking sequences may be detected, the sizes of the overlapping regions between the divided fragments may be reduced. Still further, mutations of heterozygous genes may also be detected.

BRIEF DESCRIPTION OF THE DRAWINGS

FIG. 1a represents the vector pCI-HA(URA3)-2. FIG. 1b represents BRCA1a and BRCA1b test DNA fragments, and APCa, APCb, APCC, and APCd test DNA fragments. FIG. 1c represents the operation of the present invention. FIG. 1d represents yeast transformants grown on Petri dishes.

BEST MODE FOR CARRYING OUT THE INVENTION

Figure 1A:
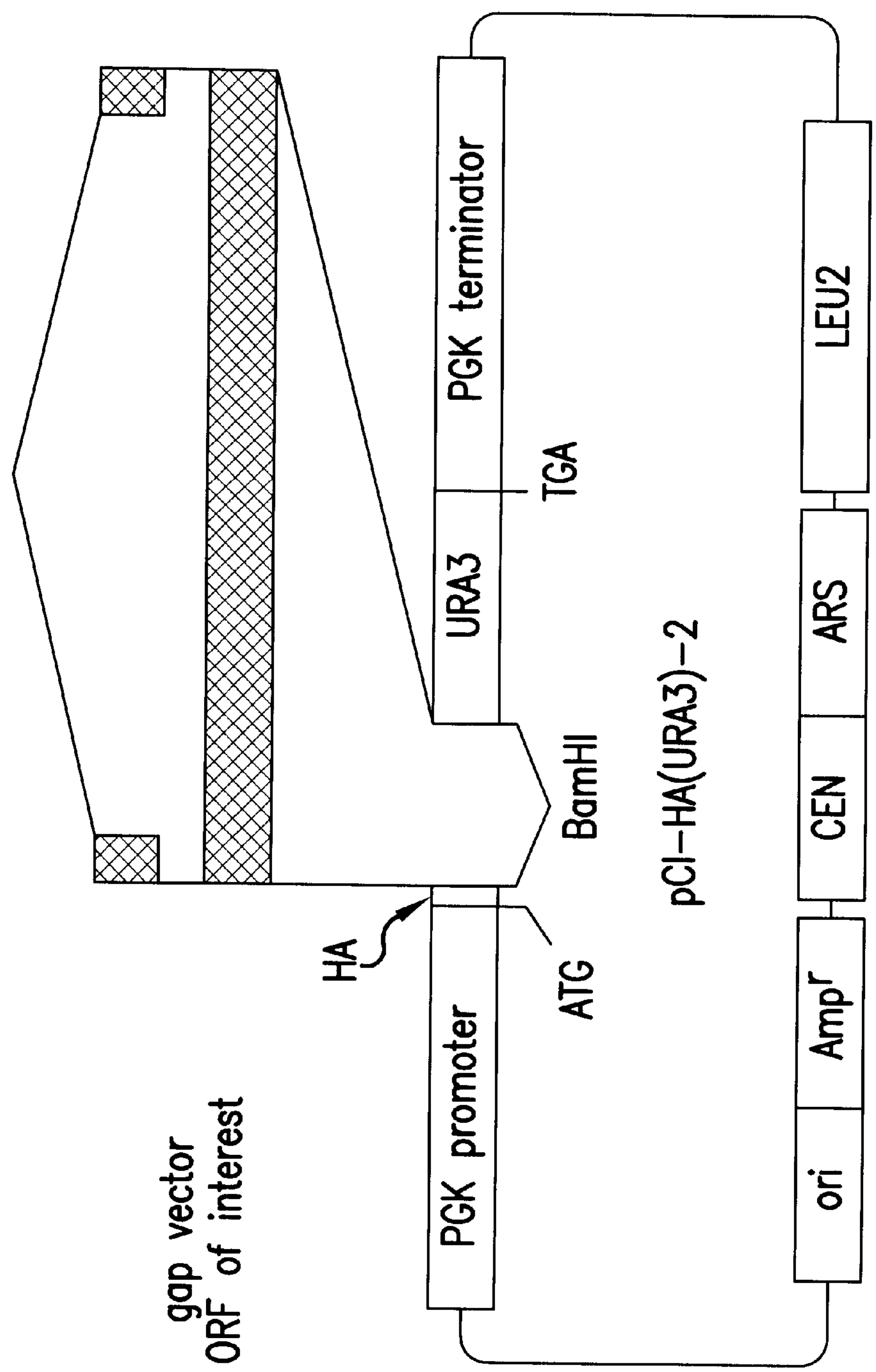
FIGS. 1a–1d are drawings for explaining the structures of the vectors used in the methods of the Examples of the present invention as well as the regions of the test DNA fragments, operations and results.

In the method of the present invention, a vector is used. The vector has a structural gene used as a reporter gene. This reporter gene encodes a polypeptide detectable based on a function thereof, and the fusion polypeptide formed by ligating the N-terminal of the polypeptide to another polypeptide is also detectable based on the function of the polypeptide encoded by the reporter gene. Examples of such a reporter gene include genes which convert auxotroph to prototroph, genes giving drug resistance, genes encoding enzymes which carry out detectable enzyme reactions and genes which convert temperature-sensitive or pH-sensitive cells to resistant cells, but the reporter gene is not restricted to these genes. Among these, genes which convert auxotroph to prototroph, and genes giving drug resistance are preferred because detection may be carried out by simply culturing transformants on a prescribed medium. In the Examples described below, the region of codon 5 and downstream thereof of URA3 gene (Alani E. et al., Genetics 117, 5–12(1987)) encoding yeast orotidine-5'-phosphate (OMP) decarboxylase is used as the reporter gene. Cells expressing this gene grow on a medium which does not contain uracil while the cells which do not express this gene cannot grow on a medium which does not contain uracil. Therefore, by employing a host auxotrophic to uracil and by culturing the transformant on a medium which does not contain uracil, whether or not the transformant expresses URA3 gene may easily be known. Further, cells expressing URA3 gene may easily be negatively selected using 5FOA (5-fluoro-orotic acid) (i.e., $Ura^{-}$is 5FOA-resistant and $Ura^{+}$is 5FOA-sensitive). Preferred examples of the reporter gene other than URA3 gene include GFP (green fluorescent protein) gene (Chalfie, M. et al., Science 236, 802–805, 1994), ADE2 gene (originated from yeast, Stotz, A. et al., Gene 95, 91–98, 1990), and CAN1 gene and CYH2 gene (both are described in Nature 387, May, 29, 1997), but the reporter gene is not restricted to these genes.

A promoter which controls the reporter gene is located upstream of the reporter gene. This promoter may be any promoter which can express the reporter gene downstream thereof in the host cell used, and known promoters may be employed. In the Examples described below, the promoter of 3-phosphoglycerate kinase (PKG) gene is used. Needless to say, however, the promoter is not restricted to this promoter. Preferred examples of the promoter other than the promoter of PKG gene include the promoters of ADH1 gene (budding yeast, Ammever, G., Methods in Enzymology, vol. 101, p.192), GAL1–GAL1D gene and of PHOS gene (both are described in Broach, J. R. et al., "Experimental Manipulation of Gene Expression" Academic Press 1983), but the promoters are not restricted to these promoters.

A translational initiation codon is located downstream of the promoter and upstream of the reporter gene. The reporter gene is translated using this translation initiation codon as its translational initiation codon. Although the translational initiation codon may exist individually, it may be contained in a second structural gene located upstream of the reporter gene. In this case, whether or not the DNA region controlled by the promoter was correctly expressed can be known by detecting the polypeptide encoded by the second structural gene by an appropriate method such as immunoassay, Western blotting or the like. This is because that when expression is correctly carried out, at least the second structural gene is expressed even when the test nucleic acid fragment contains a nonsense mutation since the test nucleic acid fragment is inserted into a site downstream of the second structural gene as hereinbelow described. The second structural gene may be any structural gene. Although hemagglutinin (HA) gene is used in the Examples described below, the second structural gene is, needless to say, not restricted to this gene.

Although the vector used in the method of the present invention may be a vector for bacteria such as *Escherichia. coli* and *Bacillus subtilis*, a vector for eukaryotic cells, especially for yeasts, into which a large gene fragment can be inserted, is preferred.

Since the vector must be replicated in the host cell, the vector has a replication origin which enables its replication in the host cell. The vector may preferably have a terminator sequence downstream of the reporter gene. Further, the vector may preferably have a selection marker such as a drug resistant gene or a gene which converts auxotroph to prototroph (in the Examples described below, LEU2 gene which converts leucine auxotroph to leucine prototroph is used). Further, in case of a vector for yeasts, the vector may preferably have CEN gene or ARS gene for stabilizing replication in a small copy number.

In the method of the present invention, a test nucleic acid fragment is inserted into a site downstream of the translational initiation codon and upstream of the reporter gene. In cases where a second structural gene exists, the test nucleic acid fragment is inserted between the second structural gene and the reporter gene. The test nucleic acid fragment may be inserted into a restriction site existing upstream of the reporter gene by a conventional method. Thus, a restriction site must exist upstream of the reporter gene. In cases where the vector used in the present invention is constructed by inserting the reporter gene and the second structural gene into an expression vector, a restriction site necessary for the insertion of the test nucleic acid fragment exist without any specific operation since the reporter gene and the second structural gene are inserted utilizing a restriction site. However, the restriction site needed for the insertion of the test nucleic acid fragment may easily be created by a conventional method.

The test nucleic acid fragment has a size that the open reading frame of the reporter gene is in-frame with the translational initiation codon when the test nucleic acid fragment is normal type. That is, when the open reading frame of the reporter gene is in-frame with the translational initiation codon before insertion of the test nucleic acid fragment, the number of the nucleotides in the test nucleic acid fragment is a multiple of 3 when the test nucleic acid fragment is normal type. This is because that if the number of the nucleotides in the test nucleic acid fragment to be inserted is a multiple of 3, frameshift does not occur. It should be noted, however, that the method of the present invention can be applied as long as the open reading frame of the reporter gene is in-frame with the translational initiation codon after a normal type DNA fragment is inserted. Therefore, the method of the present invention may be applied to those test nucleic acid fragments whose numbers of nucleotides are not a multiple of 3 when they are normal type. In this case, the open reading frame of the reporter gene and the translational initiation codon are preliminarily shifted before the insertion of the test nucleic acid fragment such that the open reading frame of the reporter gene and the translational initiation codon becomes in-frame after a normal type test nucleic acid is inserted.

The test nucleic acid fragment is not restricted at all and the test nucleic acid fragment may be any nucleic acid fragment (DNA fragment or RNA fragment) which is desired to be checked for the existence of a nonsense mutation or frameshift mutation. Although BRCA1 gene and APC gene are checked in the Examples described below, the test nucleic acid is, needless to say, not restricted to these genes. BRCA1 gene is the gene which may cause familial breast cancer and ovarian cancer when the gene is inactivated (Miki Y. et al., Science 266, 66–71 (1994), abnormality of this gene is observed in 75% of breast cancer patients), and APC gene is a gene which may cause multiple adenomatous polyp when the gene is inactivated (Kinzler K. W. et al., Science 253, 661–5 (1991), abnormality of this gene is observed in 93% of patients). Although it is not necessary to know the nucleotide sequence of the test nucleic acid fragment, the number of the nucleotides of the normal type of the test nucleic acid fragment (or at least the remainder when the number of the nucleotides of the test nucleic acid fragment is divided by 3) must be known since the open reading frame of the reporter gene must be in-frame with the translational initiation codon after the normal type test nucleic acid fragment is inserted. Therefore, as the test nucleic acid fragment, one obtained by amplifying a known gene or a part thereof by a nucleic acid amplification method such as PCR or one obtained by cutting out a fragment from a known gene or a part thereof by a restriction enzyme is usually used. It is preferred to prepare the test nucleic acid fragment by a nucleic acid amplification method such as PCR because a large number of fragment can be obtained so that sensitivity of the assay is increased.

After insertion of the test nucleic acid fragment, host cells are transformed with the obtained recombinant vector. The method for transformation per se is well-known in the art. Alternatively, host cells may be cotransformed with the test nucleic acid fragment and a gap vector cleaved at the restriction site into which the test nucleic acid fragment is to be inserted so that the desired recombinant vector having the inserted test nucleic acid fragment is constructed by homologous recombination in the host cells (see Examples below). Here, the gap vector is a vector before insertion of the test nucleic acid fragment, which has the both end regions of the test nucleic acid fragments ligated to the respective ends of the vector which ends are generated by cleavage of the vector at the restriction site into which the test nucleic acid fragment is to be inserted. By cotransforming the host with such a gap vector and the test nucleic acid fragment, since the both end regions of the test nucleic acid fragments and the regions ligated to the restriction site of the gap vector are homologous, homologous recombination occurs in the cells, so that the recombinant vector into which the test nucleic acid fragment is inserted is generated in the cells. As described in the Examples below, such a gap vector may be prepared by firstly constructing a recombinant vector into which the test nucleic acid fragment is inserted and by amplifying the region of the recombinant vector other than the test nucleic acid fragment except for the both end regions thereof. By preliminarily preparing such a gap vector in a large amount, since the test may be carried out only by the cotransformation and culturing, the test is simple, so that clinical tests may be carried out efficiently on a number of samples, which is preferred. Further, the method employing the gap vector is preferred to the method in which a ligation mixture containing the vector into which the test nucleic acid fragment has been inserted is used as it is for the transformation also because the background of $Ura^-$ is lower. The transformants may be selected depending on the selection marker.

The obtained transformants are then cultured so as to express the translational initiation codon (and the second structural gene in cases where it is contained), the inserted test nucleic acid fragment downstream thereof and the reporter gene, which are operably linked to the promoter.

As mentioned above, the test nucleic acid fragment has, if it is normal type, the size with which the open reading frame of the reporter gene is in-frame with the translational initiation codon when the test nucleic acid fragment is inserted. Therefore, in cases where the test nucleic acid fragment is normal type or has a mutation other than nonsense mutation or frameshift mutation, a fusion polypeptide having the normal polypeptide encoded by the reporter gene is produced. On the other hand, in cases where the test nucleic acid has a nonsense mutation, the region downstream of the mutated site is not expressed, so that the reporter gene is not expressed at all. In cases where the test nucleic acid fragment has a frameshift mutation, since frameshift occurs in the region downstream of the mutated site, the polypeptide encoded by the reporter gene has an amino acid sequence totally different from that of the normal polypeptide, so that it does not have the function which the normal type polypeptide has. Therefore, by determining whether or not the expressed polypeptide has the function of the normal polypeptide encoded by the reporter gene, it can be determined whether or not the test DNA fragment has a nonsense or frameshift mutation.

Whether or not the expressed polypeptide has the function which the normal polypeptide encoded by the reporter gene has may be determined by an appropriate method depending on the nature of the reporter gene. That is, in cases where the reporter gene is one which converts auxotroph to prototroph, it may be determined by employing an auxotrophic strain as the host and culturing the transformants on a medium which does not contain the required nutrition. In cases where the reporter gene is a drug resistant gene, it may be determined by employing a host which is sensitive to the drug and by culturing the transformants on the medium containing the drug. In cases where the reporter gene encodes an enzyme which performs a detectable enzyme reaction, it may be determined by adding the substrate of the enzyme so as to allow the enzyme reaction. In cases where the reporter gene converts temperature-sensitive or pH-sensitive cells to resistant cells, it may be determined by employing a sensitive strain as the host, and by culturing the transformants under a temperature or pH at which the sensitive strain cannot grow. In cases where the reporter gene encodes a fluorescent protein, it may be determined by exciting the transformants with a light having the specific wavelength and by measuring the change of the characteristics of the fluorescent wavelength.

The present invention will now be described by way of examples thereof. It should be noted that the present invention is not restricted to the examples below.

EXAMPLE 1

Detection of Nonsense Mutation or Frameshift Mutation in BRCA1 Gene (1) Construction of Gap Vector A fragment spanning nucleotide-number 423 to 1239nt of a plasmid pRS316 (Sikorski, R. S. et al., Genetics 122, 19–27 (1989), GenBank U03442, obtained from Robert S. Sikorski, Johns Hopkins University), which contains URA3 coding region from codon 5 to the natural termination codon, was amplified by PCR using a set of primers containing a BamHI site or a BglII site at the 5' end. The amplified BamHI/BglII fragment was inserted in-frame into a BamHI site of a plasmid PRSPGK (Ishioka et al., Oncogene 10, 1485–92 (1995), obtained from Chikashi ISHIOKA, Institute of Development, Aging and Cancer, Tohoku University) to produce a plasmid pCI-HA(URA3). This vector was digested by NsiI and PstI and was self-ligated to produce pCI-HA(URA3)-2 (FIG. 1*a*).

On the other hand, genomic DNAs and/or total RNAs were isolated from lymphocytes immortalized by EBV, from 9 women with early-onset breast cancer, and from lymphocytes from healthy donors as controls. The nucleotide sequences of the coding regions of BRCA1 gene of the patients and the healthy donors have been fully determined (FitzGerald, M. G. et al., New Engl. J. Med. 334, 143–9 (1996); GenBank U14680). Using a commercially available CDNA synthesis kit (First-Strand cDNA Synthesis kit (commercially available from Pharmacia), cDNAs were synthesized. Using the thus obtained genomic DNAs and cDNAs as templates, test DNA fragments were amplified by PCR. The amplified test DNA fragments were the fragment spanning 96–908nt (BRCA1a), the fragment spanning 789–4214nt (BRCA1b) and the fragment spanning 4089–5708nt (BRCA1c) (see FIG. 1*b*). BRCA1a and BRCA1c were produced by amplification using the cDNA as the template and BRCA1b was produced by amplification using each of the cDNA and genomic DNA as the template. The nucleotide sequences of the primers used for the amplification of BRCA1a were 5'-GAAAGTTCATTGGAACAGAAAGAA-3' (SEQ ID NO: 1) and 5'-ACCCTGATACTTTTCTGGATG-3' (SEQ ID NO:2). The nucleotide sequences of the primers used for the amplification of BRCA1b were 5'-CCCAGATCTGCTGCTTGTGAATTTTCTGAG-3' (SEQ ID NO:3) and 5'-CCCAGATCTTAAGTTTGAATCCATGCTTTG-3' (SEQ ID NO:4). The nucleotide sequences of the primers used for the amplification of BRCA1c were 5'-ATGAGGCATCAGTCTGAAAGC-3' (SEQ ID NO:5) and 5'-GTAGTGGCTGTGGGGGATCT-3' (SEQ ID NO:6). PCR was performed using a kit commercially available from Takara Shuzo, which was performed by firstly carrying out an initial denaturing step at 94° C. for 4 minutes, then repeating 30 times the cycle of denaturing step at 94° C. for 1 minute, annealing step at 60° C. for 1 minute and extension step at 72° C. for 3.5 minutes, and by finally carrying out an extension step at 72° C. for 4 minutes.

Amplified BRCA1a, BRCA1b and BRCA1c fragments originated from a healthy donor were respectively inserted into the BamHI site of pCI-HA(URA3)-2 to produce plasmids pCI-BR1E, pCI-BR1D and pCI-BR1G, respectively (see FIG. 1*b*). *Saccharomyces cerevisiae* YPH499 (infra) was transformed with each of these recombinant vectors. As a result, all of the transformants were $URA^+$ (transformants which can grow on a medium which does not contain uracil).

Figure 1B:
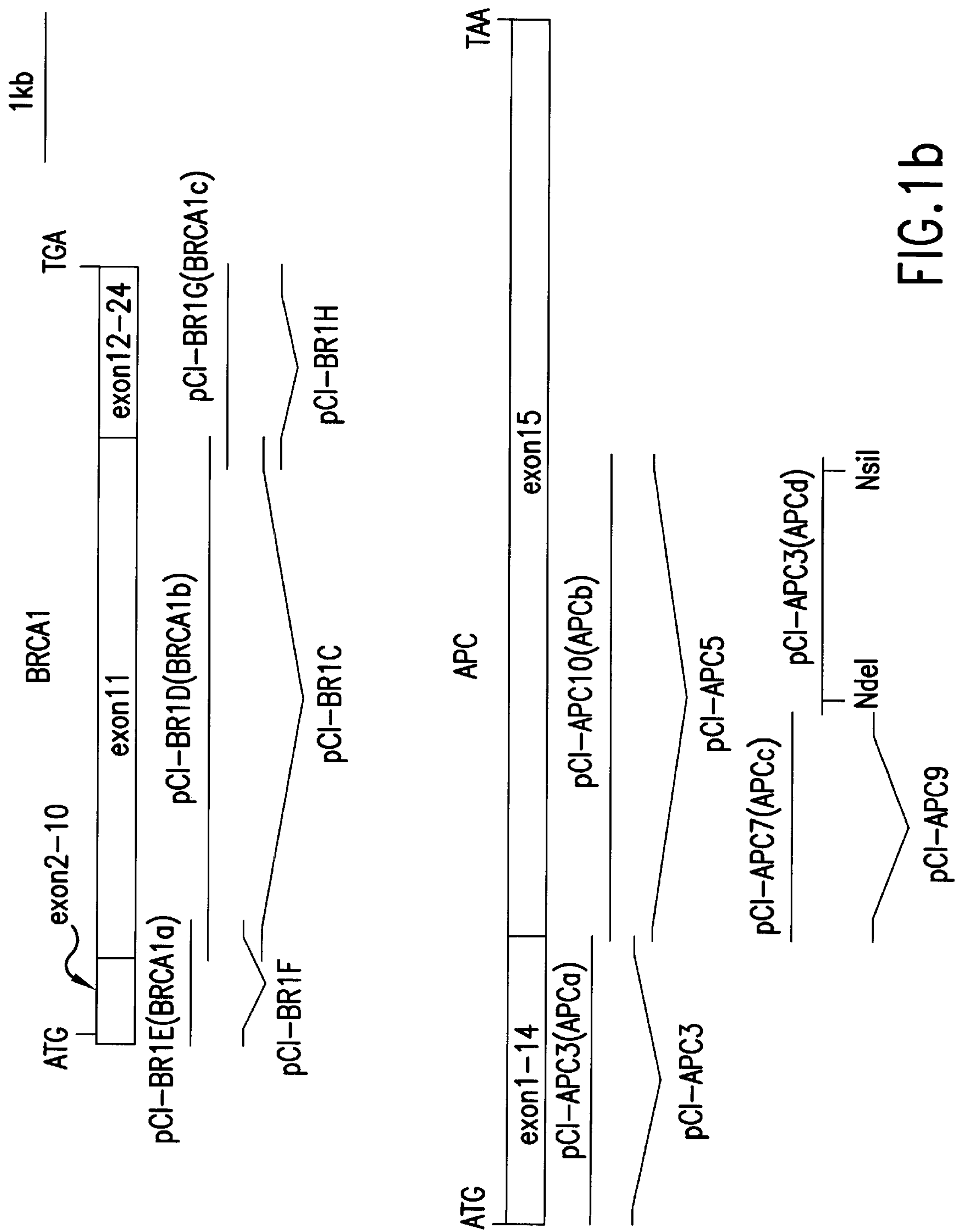
Figure 1C:
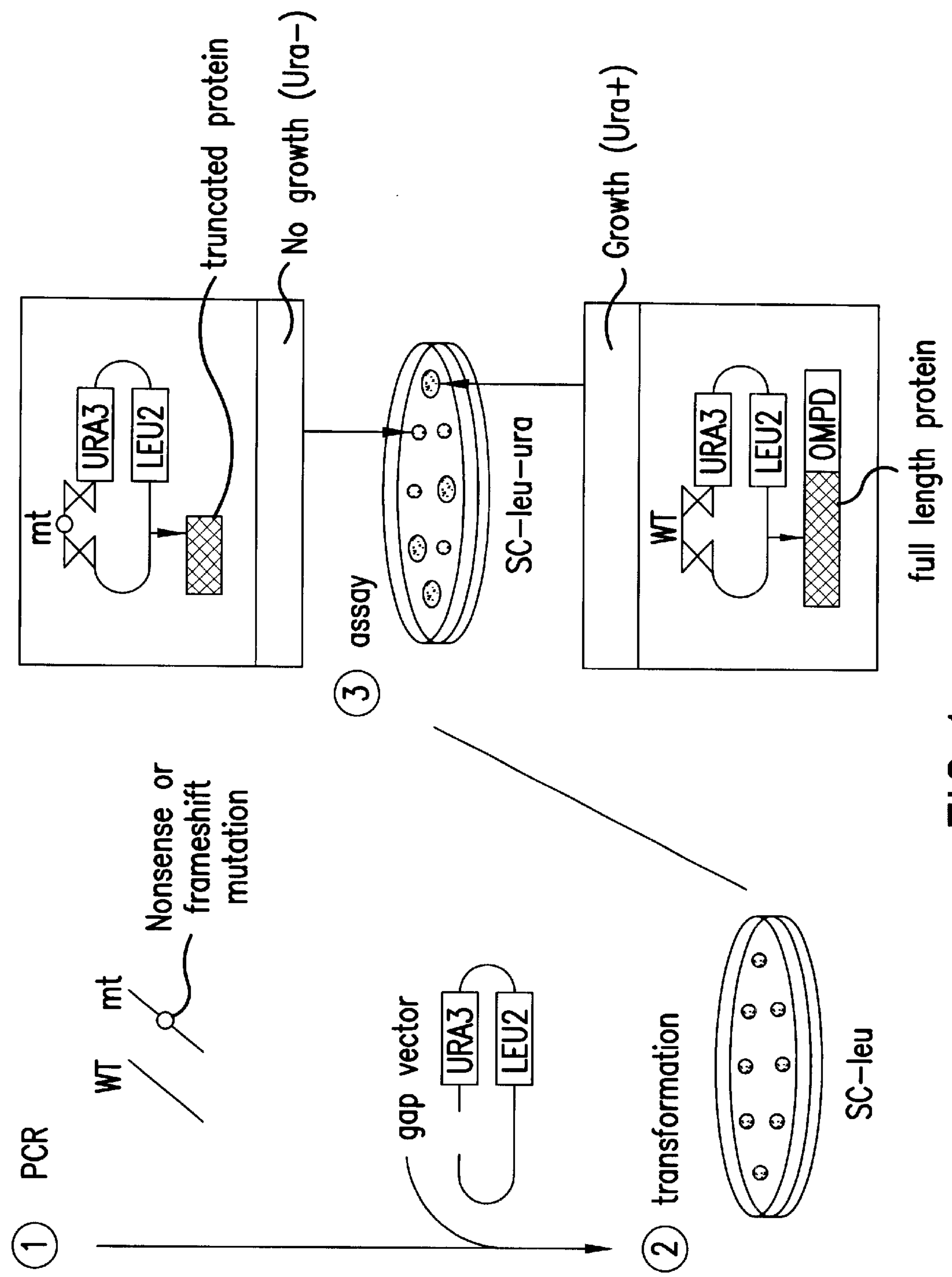

Using the obtained recombinant vectors as templates, gap vectors were prepared by PCR (FIG. 1*b*). Gap vector pCI-BR1F is one prepared by changing the 183–827nt of the insert in the plasmid pCI-BR1E to a unique (i.e., only one site exists in the vector) BglII site. Gap vector pCI-BR1C is one prepared by changing the 888–4111nt of the insert in the plasmid pCI-BR1D to a unique StuI/BamHI/SmaI site. Gap vector pCI-BR1H is one prepared by changing the 4215–5609nt of the insert in the plasmid pCI-BR1G to a unique BglII site. The nucleotide sequences of these plasmids are described in GenBank U14680. PCR was performed using the above-described full-length recombinant vector containing the insert fragment as the template, using the kit commercially available from Takara Shuzo. The nucleotide sequences of the primers used for preparing the gap vector pCI-BR1F were 5'-GAAGATCTGATTTTCTGCATAGCATTAATGAC-3' (SEQ ID NO:7) and 5'-GAAGATCTGAACATCATCAACCCAGTAATAATG-3' (SEQ ID NO:8). The nucleotide sequences of the primers used for preparing the gap vector pCI-BR1C were 5'-CCCGGATCCCGGGAGTTGGTCTGAGTGACA-3' (SEQ ID NO:9) and 5'-CCCGGATCCAGGCCTCTCAGCTGCACGCTTC-3' (SEQ ID NO:10). The nucleotide sequences of the primers used for preparing the gap vector pCI-BR1H were 5'-GAAGATCTCCTGTGGTGACCCGAGAGTGGGTG-3' (SEQ ID NO:11) and 5'-GAAGATCTATTATTTCTTCCAAGCCCGTTCC-3' (SEQ ID NO:12). PCR was performed by firstly carrying out an initial denaturing step at 94° C. for 2 minutes, then repeating 30 times the cycle of denaturing step at 94° C. for 20 seconds, annealing plus extension step at 68° C. for 10 minutes, and by finally carrying out an extension step at 68° C. for 4 minutes.

(2) Production of Transformants

As the host cell, yeast Saccharomyces cerevisiae YPH499 (commercially available from Stratagene) which is auxotrophic to leucine and uracil was used. Competent yeast cells were prepared by treating the cells cultured in YPD liquid medium with lithium acetate (LiOAc) (Ishioka C. et al., Nature Genet. 5, 124–129 (1993)). The obtained competent yeast cells were stored at −80° C. in the presence of 5% DMSO until use. Frozen competent yeast cells retain high transformation efficiency at least for three months. Cotransformation was carried out by the known LiOAc method (the method described in Ito H., J. Bacteriol. 153, 163–168 (1983) was modified as described in Ishioka H. et al., 1998 (supra)) with about 200 ng of the above-described each amplified DNA fragment (unpurified) and about 30 ng of the above-described each gap vector. For the tests of BRCA1a, BRCA1b and BRCA1c fragments, the gap vectors pCI-BR1F (BglII digest), pCI-BR1C (BamHI/SmaI digest) and pCI-BR1H (BglII digest) were used, respectively.

Transformants were selected on a synthetic complete medium which did not contain leucine. Twenty five colonies were selected from each group of the transformants and the transformants were cultured on a synthetic complete medium which did not contain leucine and uracil, thereby analyzing the uracil auxotrophy. In cases where more than 85% of transformants were $URA^+$, the test DNA fragment was judged not to contain a nonsense or frameshift mutation. In cases where all transformants were $URA^-$, the test DNA fragment was judged to contain a nonsense or frameshift mutation. In cases where the ratio of $URA^-$was small (usually 40 to 50%), the DNA fragment was judged to be a heterozygote having one which contained a nonsense or frameshift mutation and one which did not contain a nonsense or frameshift mutation.

(3) Results

Figure 1D:
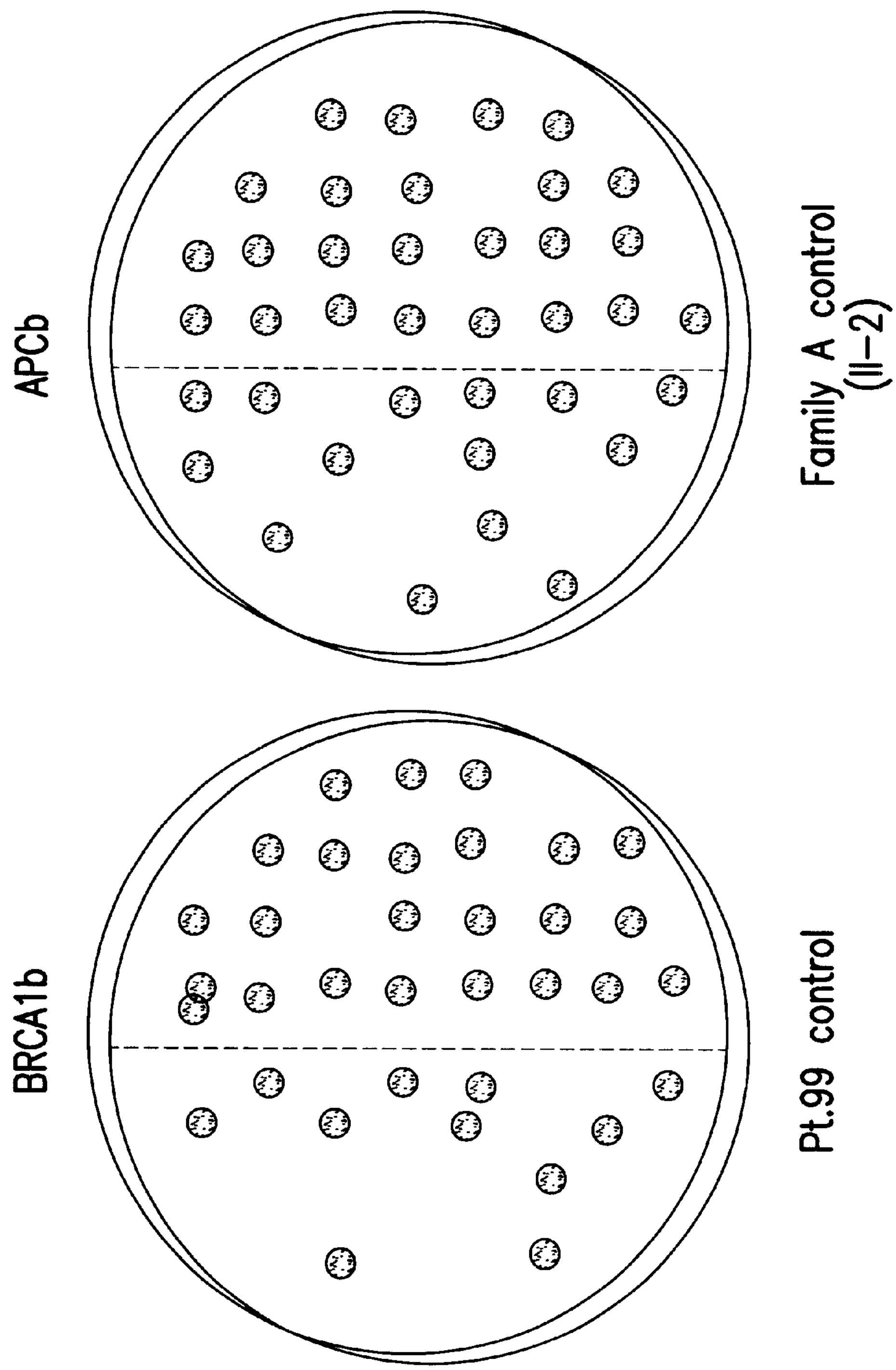

The results are shown in Table 1 below. As shown in Table 1, the results obtained by the above-described method were completely coincident with the results of the analysis of the nucleotide sequences of the test DNA fragments. Thus, it was confirmed that nonsense mutation or frameshift mutation can be detected by the method of the present invention. The results of the patient Pt.99 (see Table 1) are shown in the left side in FIG. 1*d*. The right half of the petri dish shows the results of the control in which the DNA fragment from a healthy donor was inserted and the left half shows the results of the patient Pt.99.

TABLE 1

| Patient*1 | Ratio of Ura+ Colonies (%)*2 | | | | Mutation*3 | |
|---|---|---|---|---|---|---|
| | BRCA1a | BRCA1b*4 | BRCA1b*5 | BRCA1c | Sequence | Location |
| Pt. 43 | 92 | ND | 88 | 92 | Wild Type | |
| Pt. 79 | ND | 92 | ND | ND | Wild Type | |
| Pt. 84 | 92 | 91 | 92 | 96 | Wild Type | |
| Pt. 99 | 96 | <u>44</u> | <u>48</u> | 88 | 2bp deletion (frameshift) | codon 327 (exon 11) |
| Pt. 103 | 88 | ND | 88 | 96 | Wild Type | |
| Pt. 118 | 88 | 94 | 94 | 88 | Wild Type | |
| Pt. 231 | <u>44</u> | ND | 88 | 92 | 2bp deletion (frameshift) | codon 23 (exon 2) |
| Pt. 253 | <u>48</u> | ND | 88 | 100 | 2bp deletion (frameshift) | codon 23 (exon 2) |
| Pt. 364 | 96 | ND | <u>44</u> | 92 | CGA to TGA (nonsense) | codon 563 (exon 11) |

ND: not determined
*1,*3All patients are women with breast cancer before the age 30 and have been characterized for BRCA1 mutations previously.
*2Underscored number indicates heterozygote having a gene with a nonsense or frameshift mutation and a normal gene.
*4Derived from genomic DNA of patient lymphocytes.
*5Derived from first-strand cDNA of patient lymphocytes.

EXAMPLE 2

Detection of Nonsense Mutation or Frameshift Mutation in APC Gene

By the method similar to Example 1, N-terminal side (about 61% of the entire gene) of APC genes of 6 families of patients suffering from familial multiple adenomatous polyp was analyzed. It is known that about 93% of the patients of the cancer have mutations of APC gene (Nakamura Y. et al., New Strategies for Treatment of Hereditary Colorectal Cancer, Ed. S. Baba et al., 1996, pp.93–98). Most of the mutations are located in the above-mentioned N-terminal side.

Test DNA fragments were prepared by using genomic DNA or cDNA from fresh lymphocytes from patients and a healthy donor as the templates. The amplified test DNA fragments were 19–1977nt (APCa), 1978–5256nt (APCb), 1978–3570nt (APCc) and 3571–5256nt (APCd) of APC gene (see FIG. 1*b*). The nucleotide sequences of the primers used for the amplification of APCa fragment were 5'-ATGGCTGCAGCTTCATATGAT-3' (SEQ ID NO:13) and 5'-CTGTGGTCCTCATTTGTAGC-3' (SEQ ID NO:14). The nucleotide sequences of the primers used for the amplification of APCb fragment were 5'-CAAATCCTAAGAGAGAACAAC-3' (SEQ ID NO:15) and 5'-GTCCATTATCTTTTTCACACG-3' (SEQ ID NO:16). The nucleotide sequences of the primers used for the amplification of APCc fragment were 5'-CAAATCCTAAGAGAGAACAA-3' (SEQ ID NO:17) and 5'-GGCATATTTTAAACTATAATC-3' (SEQ ID NO:18). The nucleotide sequences of the primers used for the amplification of APCd fragment were 5'-ACAGATATTCCTTCATCACAG-3' (SEQ ID NO:19) and 5'-GTCCATTATCTTTTTCACACG-3' (SEQ ID NO:20). The PCR was performed under the same conditions as in Example 1.

Amplified APCa, APCb and APCC fragments originated from healthy donor were respectively inserted into the BamHI site of pCI-HA(URA3)-2 to produce plasmids pCI-APC6, pCI-APC10 and pCI-APC7, respectively (see FIG. 1*b*). Saccharomyces cerevisiae YPH499 was transformed with each of these recombinant vectors. As a result, all of the transformants were URA+.

Using the obtained recombinant vectors as templates, gap vectors were produced by PCR (FIG. 1*b*). Gap vector pCI-APC8 is one prepared by changing the 109–1899nt of the insert in the plasmid pCI-APC6 to a unique BglII site. Gap vector pCI-APC5 is one prepared by changing the 2054–5201nt of the insert in the plasmid pCI-APC10 to a unique NsiI site. Gap vector pCI-APC9 is one prepared by changing the 2086–3489nt of the insert in the plasmid pCI-APC7 to a unique BglII site. The nucleotide sequences of these plasmids are described in GenBank M74088. The nucleotide sequences of the primers used for preparing the gap vector pCI-APC8 were 5'-CGAAGATCTATTATCTTCTAGCTCTTGTCGAAG-3' (SEQ ID NO:21) and 5'-CGAAGATCTACTTTAGCCATTATTGAAGTGGA-3' (SEQ ID NO:22). The nucleotide sequences of the primers used for preparing the gap vector pCI-APC9 were 5'-CGAAGATCTTGCTGAGAGATTCCACAAAGTTCC-3' (SEQ ID NO:23) and 5'-CGAAGATCTAGACCAACAAATTATAGCATAAAATAT-3' (SEQ ID NO:24). PCR was performed using the full-length recombinant vectors each of which contains the respective insert under the same conditions as in Example 1. Gap vector pCI-APC5 was prepared by cleaving pCI-APC10 at the two NsiI sites therein by NsiI.

Yeast *Saccharomyces cerevisiae* YPH499 was cotransformed by the same method as in Example 1 with the respective gap vector cleaved at its above-mentioned unique restriction site and the previously prepared test DNA fragment. Transformants were selected and existence of a nonsense or frameshift mutation was checked.

Figure 2:
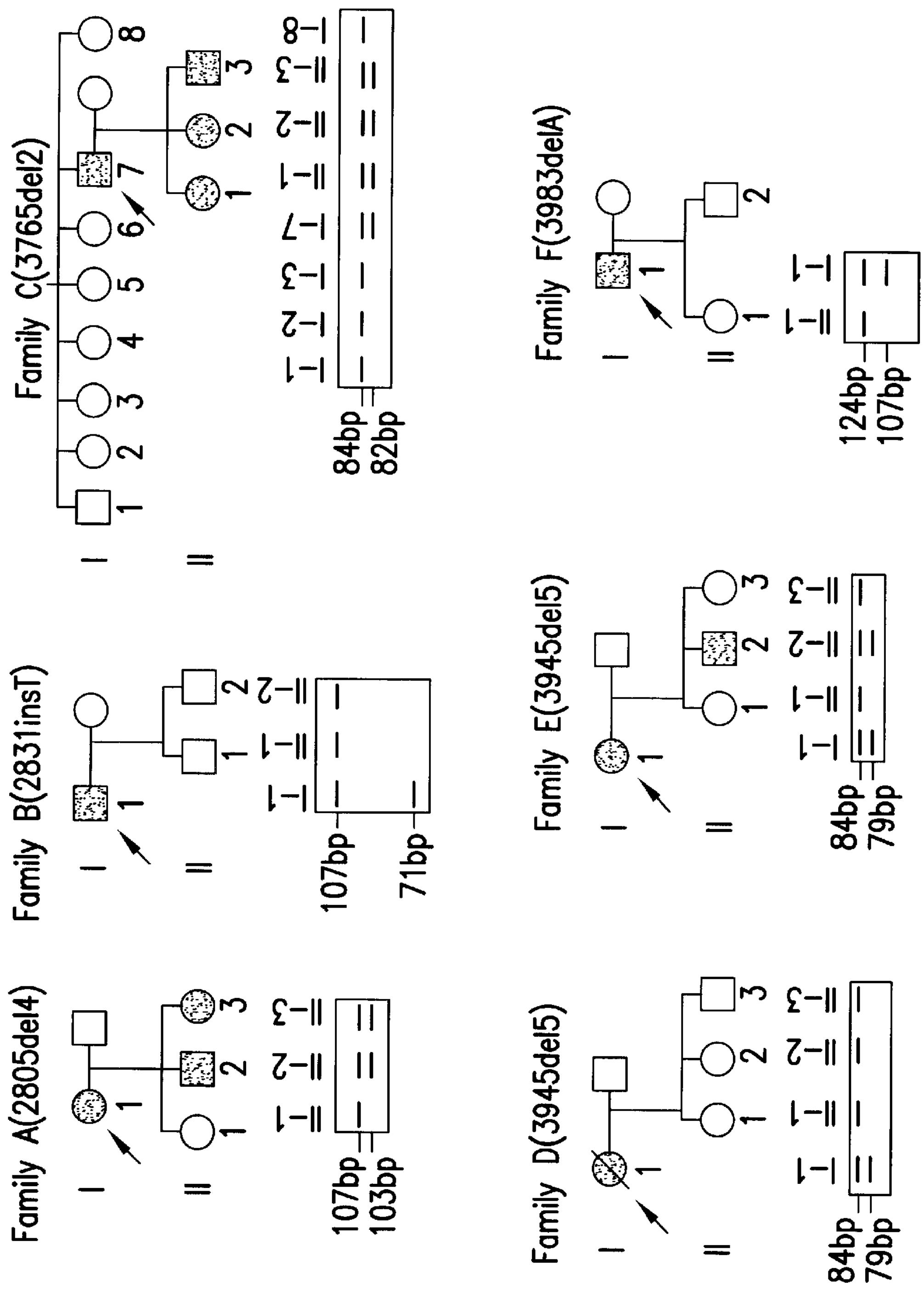
FIG. 2 shows the pedigrees of 6 families which were examined for their APC genes by the method of Example 2 according to the present invention as well as the sizes of the bands observed in electrophooresis analyzing the vicinity of the mutated sites.

The results are shown in Tables 2 and 3. In the Tables, "ND" means "not determined." All individuals in the 6 families of familial multiple adenomatous polyp are Japanese. The underscored number in the columns of the Tables indicates a heterozygote having a gene with a nonsense or frameshift mutation and a normal gene. The underscored nucleotides in the "Sequence" column of the Tables were deleted or inserted. Pedigrees of the tested 6 families are shown in FIG. 2. In FIG. 2, the individuals indicated by solid symbols are those in whom a nonsense or frameshift mutation was detected. As shown in Tables 2 and 3, the results obtained by the above-described method were completely coincident with the results of the analysis of the nucleotide sequences of the test DNA fragments. Thus, it was confirmed that nonsense mutation or frameshift mutation can be detected by the method of the present invention. The results of the patient II-2 (see Table 2) in Family A are schematically shown in the right side in FIG. 1*d*. The right half of the Petri dish shows the results of the control in which the DNA fragment from the healthy donor was inserted and the left half shows the results of the patient II-2 in Family A.

deletion at 2805nt (2805del4). Only 107 bp fragment was observed in II-1.

Family B

The identical PCR product with Family A was digested by AflII. In addition to a normal-sized (107 bp) fragment, a 71 bp fragment was observed in the proband, I-1, because

TABLE 2

| FAP | Ratio of $Ura^+$ Colony (%)*[2] | | | Mutation | | | |
|---|---|---|---|---|---|---|---|
| Family*[1] | APCb | APCc | APCd | Location | Sequence*[3] | Consequence | Name |
| Family A | | | | | | | |
| II-1 | 100 | 92 | ND | | | | |
| II-2 | 38 | 48 | 92 | codon 929–930 (Exon 15) | CATACA→CA | Frameshift | 2805del4 |
| II-3 | 56 | 48 | ND | | | | |
| Family B | | | | | | | |
| I-1 | 50 | 44 | 100 | codon 938 (Exon 15) | ACTAAG→ACTTAG | Frameshift | 2831insT |
| II-1 | 96 | 92 | ND | | | | |
| II-2 | 88 | 100 | ND | | | | |
| Family C | | | | | | | |
| I-1 | ND | ND | 100 | | | | |
| I-2 | ND | ND | 100 | | | | |
| I-3 | ND | ND | 96 | | | | |
| I-7 | 40 | 92 | 56 | codon 1249–1250 (Exon 15) | TGCAAA→TGA | Nonsense | 3765del2 |
| I-8 | ND | ND | 92 | | | | |
| II-1 | ND | ND | 40 | | | | |
| II-2 | ND | ND | 48 | | | | |
| II-3 | ND | ND | 52 | | | | |

TABLE 3

| FAP | | | | Mutation | | | |
|---|---|---|---|---|---|---|---|
| Family*[1] | APCb | APCc | APCd | Location | Sequence*[3] | Consequence | Name |
| Family D | | | | | | | |
| I-1 | 60 | 92 | 56 | codon 1309–1311 (Exon 15) | GAAAAGATT→GATT | Frameshift | 3945del5 |
| II-1 | ND | ND | 92 | | | | |
| II-2 | ND | ND | 96 | | | | |
| II-3 | ND | ND | 88 | | | | |
| Family E | | | | | | | |
| I-1 | 44 | 96 | 48 | codon 1309–1311 (Exon 15) | GAAAAGATT→GATT | Frameshift | 3945del5 |
| II-1 | ND | ND | 92 | | | | |
| II-2 | ND | ND | 48 | | | | |
| II-3 | ND | ND | 92 | | | | |
| Family F | | | | | | | |
| I-1 | 57 | 92 | 48 | codon 1322 (Exon 15) | GAA→GA | Frameshift | 3983delA |
| II-1 | ND | ND | 92 | | | | |

ND: not determined
*[1]All individuals in the 6 families of familial multiple adenomatous polyp are Japanese.
*[2]Underscored number indicates heterozygote having a gene with a nonsense or frameshift mutation and a normal gene.
*[3]Underscored nucleotides were deleted or inserted.

Each region around the mutated site was amplified by PCR. The PCR product was electrophoresed in 16% polyacrylamide gel and was visualized by ethidium bromide staining and analyzed. The size of each band obtained for each family is shown below each family in the pedigree shown in FIG. 2. The results of each family will now be described.

Family A

Amplification of APC fragment spanning 2761–2877nt (GenBank M74088) generated an abnormally short (103 bp) fragment as well as a normal-sized (107 bp) fragment in affected siblings, II-2 and II-3 because of heterozygous 4 bp insertion of T at 2831nt (2831insT) generates an AflII site, CTTAAG. This additional band was not found in II-1 and II-2.

Family C

Amplification of APC fragment spanning 3744–3827nt generated an abnormally short 82 bp fragment as well as a normal-sized 84 bp fragment in the proband, I-7 and three affected members (II-1, II-2 and II-3) because of heterozygous 2 bp deletion at 3765nt (3765del2). The additional band was not observed in other unaffected members.

Families D and E

Amplification of APC fragment spanning 3881–3964nt generated an abnormally short (79 bp) fragment as well as a normal-sized (84 bp) fragment in the probands, I-1 (both Families D and E) and an affected member, II-2 (Family E), because of heterozygous 5 bp deletion at 3945nt (3945del5). Only normal-sized product was observed in II-1 (both Families D and E), II-2 (Family D) and II-3 (both Families D and E).

Family F

The APC fragment spanning 3881–4004nt was amplified using a mismatch primer 5'-TGCTGTGACACTGCTGGAGC-3' (SEQ ID NO:25) (the underscored G is the mismatch nucleotide) to generate T to C change at 3986nt and was digested by SacI. In addition to a normal-sized (124 bp) fragment, a 107 bp fragment was observed in the proband, I-1, because 1 bp deletion at 3983nt (3983delA) combined with the T to C change generates a SacI, GAGCTC. The 107 bp band was not observed in II-1.

EXAMPLE 3

Detection of Nonsense Mutation or Frameshift Mutation in BRCA2 Gene (1) Construction of BRCA2 Gap Vector A fragment spanning 423–1239nt of a plasmid pRS316 (Sikorski, R. S. et al., Genetics 122, 19–27 (1989), GenBank U03442, obtained from Robert S. Sikorski, Johns Hopkins University), which contains URA3 coding region from codon 5 to the natural termination codon, was amplified by PCR using a set of primers containing a BamHI site or a BglII site at the 5' end. The amplified BamHI/BglII fragment was inserted in-frame into a BamHI site of a plasmid pRSPGK (Ishioka et al., Oncogene 10, 1485–92 (1995), obtained from Chikashi ISHIOKA, Institute of Development, Aging and Cancer, Tohoku University) to produce a plasmid pCI-HA(URA3). This vector was digested by NsiI and PstI and was self-ligated to produce pCI-HA(URA3)-2 (FIG. 1*a*).

Figure 3:
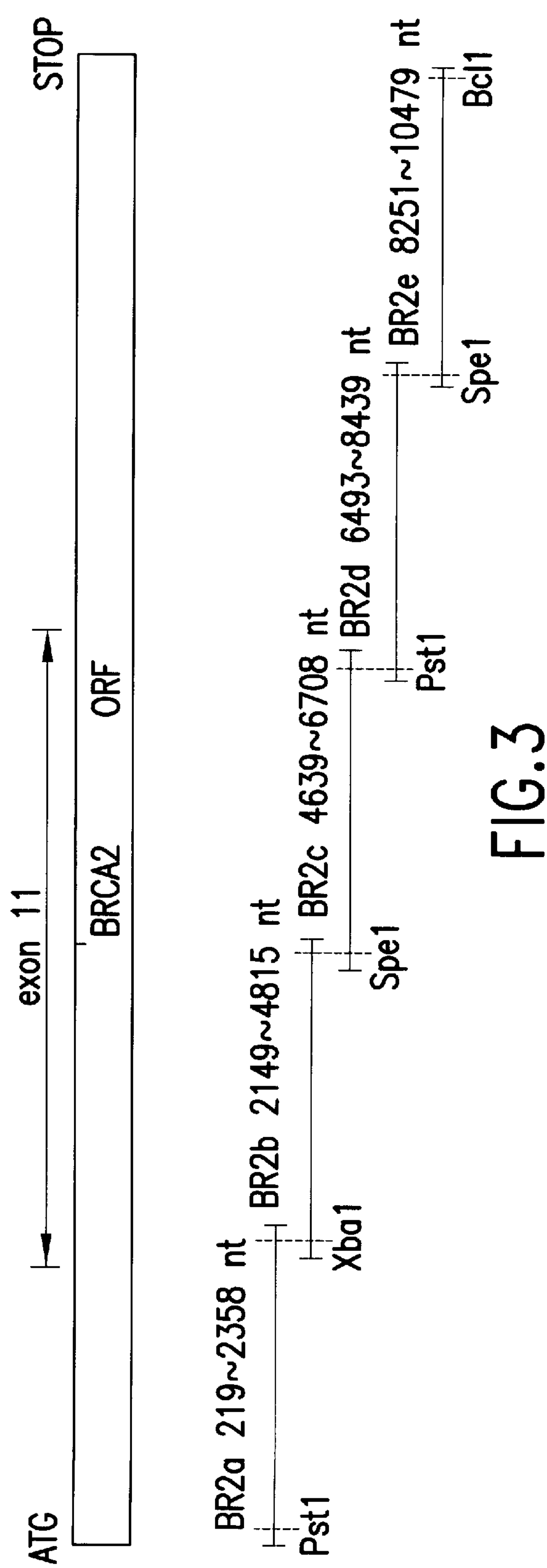
FIG. 3 shows arrangements of the regions in the BRCA2 gene, which were used as the test nucleic acid fragments in Example 3 of the present invention, as well as the restriction sites.

On the other hand, BR2a, BR2b, BR2c, BR2d and BR2e fragments originated from a healthy donor were amplified by PCR under the conditions described below. The arrangements of these fragments and restriction sites are shown in FIG. 3. The amplified DNA fragments were 219–2358nt (BR2a), 2149–4815nt (BR2b), 4639–6708nt (BR2c), 6493–8439nt (BR2d) and 8251–10476nt (BR2e) of BRCA2 gene. The nucleotide sequences of the primers used for the amplification of BR2a fragment were 5'-GGAAGATCTATGCCTATTGGATCCAAAGAGAG-3' (SEQ ID NO:26) and 5'-GGAAGATCTTGACAGAATCAGCTTCTGGGG-3' (SEQ ID NO:27). The nucleotide sequences of the primers used for the amplification of BR2b fragment were 5'-CGGGATCCTCTTCTGTGAAAAGAAGCTGTTCAC-3' (SEQ ID NO:28) and 5'-CGGGATCCCCCGCTAGCTGTATGAAAACCC-3' (SEQ ID NO:29). The nucleotide sequences of the primers used for the amplification of BR2c fragment were 5'-CGGGATCCAGAAAGAACAAAATGGACATTCTAAG-3' (SEQ ID NO:30) and 5'-CGGGATCCTTGTTGAAATTGAGAGAGATATGGAG-3' (SEQ ID NO:31). The nucleotide sequences of the primers used for the amplification of BR2d fragment were 5'-GGAAGATCTGAGCATAGTCTTCACTATTCACCTAC-3' (SEQ ID NO:32) and 5'-GGAAGATCTTAAGAGGGGAGGATCTAACTGG-3' (SEQ ID NO:33). The nucleotide sequences of the primers used for the amplification of BR2e fragment were 5'-CGGGATCCGATAGAAGCAGAAGATCGGCTATAA-3' (SEQ ID NO:34) and 5'-CGGGATCCGATATATTTTTTAGTTGTAATTGTGTCCTG-3' (SEQ ID NO:35). The PCR for BR2a was performed by firstly carrying out an initial denaturing step at 94° C. for 4 minutes, then repeating 35 times the cycle of denaturing step at 94° C. for 30 seconds and annealing+extension step at 68° C. for 3 minutes (the annealing+extension step is prolonged for 4 seconds per cycle), and by finally carrying out an extension step at 72° C. for 5 minutes. The PCR for BR2b and BR2c was performed by firstly carrying out an initial denaturing step at 94° C. for 4 minutes, then repeating 27 times the cycle of denaturing step at 94° C. for 30 seconds, annealing step at 60° C. for 15 seconds and extension step at 72° C. for 3 minutes+DT 4 seconds, and by finally carrying out an extension step at 72° C. for 5 minutes. The PCR for BR2d was performed by firstly carrying out an initial denaturing step at 94° C. for 4 minutes, then repeating 35 times the cycle of denaturing step at 94° C. for 30 seconds, annealing step at 60° C. for 15 seconds and extension step at 72° C. for 3 minutes+DT 4 seconds, and by finally carrying out an extension step at 72° C. for 5 minutes. The PCR for BR2e was performed by firstly carrying out an initial denaturing step at 94° C. for 2 minutes, then repeating 35 times the cycle of denaturing step at 94° C. for 30 seconds, annealing step at 58° C. for 30 seconds and extension step at 72° C. for 3 minutes+DT 4 seconds, and by finally carrying out an extension step at 72° C. for 5 minutes.

Amplified BR2a, BR2b, BR2c, BR2d and BR2e fragments originated from a healthy donor were respectively inserted into the BamHI site of pCI-HA(URA3)-2 to produce plasmids pBR2a, pBR2b, pBR2c, pBR2d and pBR2e. Saccharomyces cerevisiae YPH499 was transformed with each of these recombinant vectors. As a result, all of the transformants were URA$^+$.

A gap vector of pBR2a was prepared by digesting the recombinant vector pBR2a by restriction enzymes PstI and XbaII so as to remove the central region, 365–2239nt, of the insert. A gap vector of pBR2b was prepared by digesting the recombinant vector pBR2b by restriction enzymes XbaI and SpeI so as to remove the central region, 2239–4734nt, of the insert. A gap vector of pBR2c was prepared by digesting the recombinant vector pBR2c by restriction enzymes SpeI and PstI so as to remove the central region, 4734–6603nt, of the insert. A gap vector of pBR2d was prepared by digesting the recombinant vector pBR2d by restriction enzymes PstI and SpeI so as to remove the central region, 6603–8350nt, of the insert. A gap vector of pBR2e was prepared by digesting the recombinant vector pBR2e by restriction enzymes SpeI and BclI so as to remove the central region, 8350–10397nt, of the insert. The nucleotide sequences of these gap vectors are described in GenBank U43746.

(2) BRCA2 SC Assay

Entire regions of the open reading frames of 2 early-onset breast cancer patients and a healthy donor were analyzed.

Genomic DNAs and/or total RNAs were isolated from lymphocytes immortalized by EBV, from 2 women with early-onset breast cancer, and from lymphocytes from a healthy donor as a control. The nucleotide sequences of the coding regions of BRCA2 gene of the patients and the healthy donor are known. Using a commercially available CDNA synthesis kit (First-Strand cDNA Synthesis kit (commercially available from Pharmacia), cDNAs were synthesized. Using the thus obtained genomic DNAs and cDNAs as templates, test DNA fragments were amplified by PCR. The amplified test DNA fragments were the fragments spanning 219–2358nt (BR2a), 2149–4815nt (BR2b), 4639–6708nt (BR2c), 6493–8439nt (BR2d) and 8251–10476nt (BR2e), respectively. The nucleotide sequences of the primers used for the amplification of BR2a were 5'-ATGCCTATTGGATCCAAAGAGAG-3' (SEQ ID NO:36) and 5'-TGACAGAATCAGCTTCTGGGG-3' (SEQ ID NO:37). The nucleotide sequences of the primers used for the amplification of BR2b were 5'-TCTTCTGTGAAAAGAAGCTGTTCAC-3' (SEQ ID NO:38) and 5'-CCCGCTAGCTGTATGAAAACCC-3' (SEQ ID NO:39). The nucleotide sequences of the primers used for the amplification of BR2c were 5'-AGAAAGAACAAAATGGACATTCTAAG-3' (SEQ ID NO:40) and 5'-TTGTTGAAATTGAGAGAGATATGGAG-3' (SEQ ID NO:41). The nucleotide sequences of the primers used for the amplification of BR2d were 5'-TCTGAGCATAGTCTTCACTATTCACCTAC-3' (SEQ ID NO:42) and 5'-TCTTAAGAGGGGAGGATCTAACTGG-3' (SEQ ID NO:43). The nucleotide sequences of the primers used for the amplification of BR2e were 5'-GATAGAAGCAGAAGATCGGCTATAA-3' (SEQ ID NO:44) and 5'-GATATATTTTTAGTTGTAATTGTGTCCTG-3' (SEQ ID NO:45). The PCR for BR2a was performed by firstly carrying out an initial denaturing step at 94° C. for 4 minutes, then repeating 35 times the cycle of denaturing step at 94° C. for 30 seconds and annealing+extension step at 68° C. for 3 minutes+DT 4 seconds, and by finally carrying out an extension step at 72° C. for 5 minutes. The PCR for BR2b and BR2c was performed by firstly carrying out an initial denaturing step at 94° C. for 4 minutes, then repeating 27 times the cycle of denaturing step at 94° C. for 30 seconds, annealing step at 60° C. for 15 seconds and extension step at 72° C. for 3 minutes+DT 4 seconds, and by finally carrying out an extension step at 72° C. for 5 minutes. The PCR for BR2d was performed by firstly carrying out an initial denaturing step at 94° C. for 4 minutes, then repeating 35 times the cycle of denaturing step at 94° C. for 30 seconds, annealing step at 60° C. for 15 seconds and extension step at 72° C. for 3 minutes+DT 4 seconds, and by finally carrying out an extension step at 72° C. for 5 minutes. The PCR for BR2e was performed by firstly carrying out an initial denaturing step at 94° C. for 4 minutes, then repeating 35 times the cycle of denaturing step at 94° C. for 30 seconds, annealing step at 58° C. for 30 seconds and extension step at 72° C. for 3 minutes+DT 4 seconds, and by finally carrying out an extension step at 72° C. for 5 minutes.

(3) Detection

Yeast *Saccharomyces cerevisiae* YPH499 was cotransformed by the same method as in Examples 1 and 2 with the respective gap vector cleaved at the above-mentioned unique restriction site and the previously prepared test DNA fragment. Transformants was selected and existence of a nonsense or frameshift mutation was checked. Selection of the transformants was performed by using a uracil auxotroph as a host and 1) by culturing the transformants on a medium not containing uracil so as to positively select the transformants, and 2) by culturing the transformants on a medium containing 5FOA (5-fluoro-orotic acid) so as to negatively select the transformants.

(4) Results

The results are shown in Table 4. DNA sequence analysis was carried out for Patient 1 and Patient 2. In Patient 1, heterozygous 5146delTTTA (4 bp deletion) was detected in BR2c fragment. In Patient 2, heterozygous 6697delTC (2 bp deletion) was detected in BR2d fragment. Thus, the results obtained by the above-described method were completely coincident with the results of the analysis of the nucleotide sequences of the test DNA fragments. Thus, it was confirmed that nonsense mutation or frameshift mutation can be detected by the method of the present invention.

TABLE 4

| | BR2a | BR2b | BR2c | BR2d | BR2e |
|---|---|---|---|---|---|
| Healthy Donor Control 1 | 88% / 8% | 92% / 6% | 94% / 4% | 90% / 10% | 84% / |
| Healthy Donor Control 2 | 92% / 10% | 92% / 12% | 92% / 4% | 86% / 8% | 86% / |
| Patient 1 | 86% / 14% | 92% / 6% | 40% / 56% | 84% / 12% | 90% / 12% |
| Patient 2 | 88% / 12% | 100% / 4% | 92% / 0% | 38% / 60% | 88% / 6% |

% $Ura^+$/ % $5FOA^+$

EXAMPLE 4

Detection of Nonsense Mutation or Frameshift Mutation in hMSH2 Gene (1) Construction of hMSH2 Gap Vector Full-length region of the open reading frame of hMSH2 (4–2805nt of GenBank U03911) originated from a healthy donor, which was amplified by PCR, was inserted into the BamHI site of pCI-HA(URA3)-2 to produce pCI-MS19. Saccharomvces cerevisiae YPH499 was transformed with the recombinant vector by a conventional method. All of the obtained transformants were URA and 5FOA-sensitive.

Figure 4:
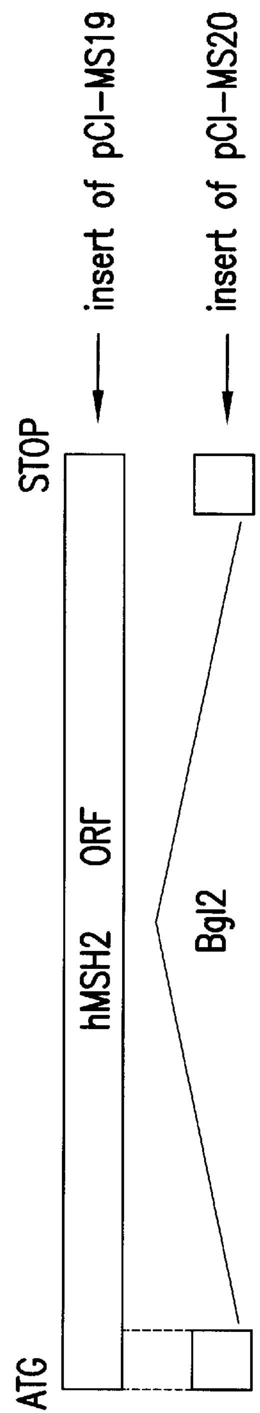
FIG. 4 shows the structures of the inserts in the recombinant vectors pCI-MS19 and pCI-MS20, which were used as test nucleic acid fragments in Example 4 of the present invention.

A gap vector pCI-MS20 was prepared by digesting the recombinant vector pCI-MS19 by restriction enzyme BglII so as to remove the central region, 97–2730nt, of the insert. The structures of the inserts in the recombinant vectors pCI-MS19 and pCI-MS20 are shown in FIG. 4.

(2) hMSH2 SC Assay

Entire regions of the open reading frame of hMSH2 genes of one patient suffering from hereditary non-polyposis colon cancer and of two healthy donors were analyzed.

Total RNAs were isolated from lymphocytes of one patient suffering from hereditary non-polyposis colon cancer and of two healthy donors were isolated. The nucleotide sequences of the coding regions of hMSH2 gene of the patients and the healthy donors are known. Using a commercially available cDNA synthesis kit (First-Strand cDNA Synthesis kit (commercially available from Pharmacia), cDNAs were synthesized. Using the thus obtained cDNAs as templates, test DNA fragments were amplified by PCR. The amplified test DNA fragments were the fragments spanning 4–2805nt of hMSH2 gene. The nucleotide sequences of the primers used for the amplification of fragments were 5'-ATGGCGGTGCAGCCGAAGGAGACGC-3' (SEQ ID NO:46) and 5'-CGTAGTAACTTTTATTCGTGAAATGATTTCATT 3' (SEQ ID NO:47). The PCR was performed by firstly carrying out an initial denaturing step at 94° C. for 4 minutes, then repeating 32 times the cycle of denaturing step at 94° C. for 30 seconds, annealing step at 60° C. for 30 seconds and extension step at 72° C. for 3 minutes, and by finally carrying out an extension step at 72° C. for 5 minutes.

(3) Detection

Yeast *Saccharomyces cerevisiae* YPH499 was cotransformed by the same method as in Examples 1, 2 and 3 with the gap vector cleaved at its above-mentioned unique restriction site and the previously prepared test DNA fragment.

Transformants were selected and existence of a nonsense or frameshift mutation was checked. Selection of the transformants was performed by using a uracil auxotroph as a host and 1) by culturing the transformants on a medium not containing uracil so as to positively select the transformants, and 2) by culturing the transformants on a medium containing 5FOA (5-fluoro-orotic acid) so as to negatively select the transformants.

(4) Results

The results are shown in Table 5. DNA sequence analysis was carried out for Patient 1. In Patient 1, heterozygous 2297delC (1 bp deletion) was detected in hMSH2 fragment. Thus, the results obtained by the above-described method were completely coincident with the results of the analysis of the nucleotide sequences of the test DNA fragments. Thus, it was confirmed that nonsense mutation or frameshift mutation can be detected by the method of the present invention.

TABLE 5

| | % $Ura^+$ | % $5FOA^+$ |
|---|---|---|
| Healthy Donor Control 1 | 86% | 14% |
| Healthy Donor Control 2 | 92% | 8% |
| Patient | 40% | 60% |

What is claimed is:

1. A method for detecting nonsense mutations and frameshift mutations in a test nucleic acid fragment, comprising the steps of:

inserting a test nucleic acid fragment which may contain a frameshift mutation or a nonsense mutation or both into a site of a vector having a promoter, a translational initiation codon downstream of said promoter, a reporter gene which is a structural gene located downstream of said translational initiation codon, which is operably linked to said promoter, which encodes a polypeptide, in cases where a fusion polypeptide is formed, said fusion polypeptide being detectable based on a function of said polypeptide encoded by said reporter gene, said site into which said test nucleic acid fragment is inserted being located downstream of said translational initiation codon and upstream of said reporter gene, said test nucleic acid fragment being one which allows, when inserted, in-frame location of said reporter gene with respect to said translational initiation codon when said test nucleic acid is normal type;

expressing said test nucleic acid fragment and said reporter gene downstream thereof in the resulting recombinant vector in a host cell; and determining whether said fusion polypeptide having said function of said polypeptide encoded by said reporter gene is produced or not, non-production of said fusion protein having said function of said polypeptide encoded by said reporter gene being indicative that said test nucleic acid contains a nonsense mutation or a frameshift mutation or both, wherein said host cell is selected from the group consisting of: an auxotrophic host cell, a temperature-sensitive host cell, a pH-sensitive host cell, and a drug-sensitive host cell and said reporter gene is Uracil 3 (URA3) gene.

2. The method according to claim 1, wherein said translational initiation codon is contained in a second structural gene located upstream of said reporter gene and said test nucleic acid fragment is inserted between said second structural gene and said reporter gene and said second structural gene is a hemagglutinin gene.

3. The method according to claim 1 or 2, wherein said host cell is a yeast cell.

4. The method according to claim 3, wherein said yeast is *Saccharomyces cerevisiae.*

5. The method according to claim 1 or 2, wherein said test nucleic acid fragment is Breast Cancer 1 (BRCA1) gene or a fragment thereof.

6. The method according to claim 1 or 2, wherein said test nucleic acid fragment is Adenomatous Polyposis Coli (APC) gene or a fragment thereof.

7. The method according to claim 1 or 2, wherein said test nucleic acid fragment is Breast Cancer 2 (BRCA2) gene or a fragment thereof.

8. The method according to claim 1 or 2 wherein said test nucleic acid fragment is Human MutS Homologue 2 gene or a fragment thereof.

* * * * *

SEQUENCE LISTING

```
<160> NUMBER OF SEQ ID NOS: 47

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 1

gaaagttcat tggaacagaa agaa                                          24


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2

accctgatac ttttctggat g                                             21


<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 3

cccagatctg ctgcttgtga attttctgag                                    30


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 4

cccagatctt aagtttgaat ccatgctttg                                    30


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:primer
```

-continued

<400> SEQUENCE: 5
atgaggcatc agtctgaaag c 21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
gtagtggctg tgggggatct 20

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 7
gaagatctga ttttctgcat agcattaatg ac 32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 8
gaagatctga acatcatcaa cccagtaata atg 33

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 9
cccggatccc gggagttggt ctgagtgaca 30

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 10
cccggatcca ggcctctcag ctgcacgctt c 31

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 11
gaagatctcc tgtggtgacc cgagagtggg tg 32

<210> SEQ ID NO 12
<211> LENGTH: 32

-continued

```
<212> TYPE: DNA
<213> ORGANISM: Artificial Sequence
<220> FEATURE:
<223> OTHER INFORMATION: Description of Artificial Sequence:primer

<400> SEQUENCE: 12

gaagatctat tattttcttc caagcccgtt cc                                 32


<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 13

atggctgcag cttcatatga t                                             21


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 14

ctgtggtcct catttgtagc                                               20


<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 15

caaatcctaa gagagaacaa c                                             21


<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 16

gtccattatc tttttcacac g                                             21


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 17

caaatcctaa gagagaacaa                                               20


<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 18
```

-continued

```
ggcatatttt aaactataat c                                             21


<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 19

acagatattc cttcatcaca g                                             21


<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 20

gtccattatc tttttcacac g                                             21


<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 21

cgaagatcta ttatcttcta gctcttgtcg aag                                33


<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 22

cgaagatcta ctttagccat tattgaagtg ga                                 32


<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 23

cgaagatctt gctgagagat tccacaaagt tcc                                33


<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 24

cgaagatcta gaccaacaaa ttatagcata aaatat                             36


<210> SEQ ID NO 25
<211> LENGTH: 20
<212> TYPE: DNA
<213> ORGANISM: Artificial Sequence
```

-continued

<220> FEATURE:
<223> OTHER INFORMATION: Description of Artificial Sequence:primer

<400> SEQUENCE: 25
tgctgtgaca ctgctggagc 20

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 26
ggaagatcta tgcctattgg atccaaagag ag 32

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 27
ggaagatctt gacagaatca gcttctgggg 30

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 28
cgggatcctc ttctgtgaaa agaagctgtt cac 33

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 29
cgggatcccc cgctagctgt atgaaaaccc 30

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 30
cgggatccag aaagaacaaa atggacattc taag 34

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 31
cgggatcctt gttgaaattg agagagatat ggag 34

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 32
ggaagatctg agcatagtct tcactattca cctac 35

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 33
ggaagatctt aagaggggag gatctaactg g 31

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 34
cgggatccga tagaagcaga agatcggcta taa 33

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 35
cgggatccga tatatttttt agttgtaatt gtgtcctg 38

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 36
atgcctattg gatccaaaga gag 23

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 37
tgacagaatc agcttctggg g 21

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:primer -continued

<400> SEQUENCE: 38
tcttctgtga aaagaagctg ttcac 25

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 39
cccgctagct gtatgaaaac cc 22

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 40
agaaagaaca aaatggacat tctaag 26

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 41
ttgttgaaat tgagagagat atggag 26

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 42
tctgagcata gtcttcacta ttcacctac 29

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 43
tcttaagagg ggaggatcta actgg 25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 44
gatagaagca gaagatcggc tataa 25

<210> SEQ ID NO 45

-continued

```
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 45

gatatatttt ttagttgtaa ttgtgtcctg                                   30


<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 46

atggcggtgc agccgaagga gacgc                                        25


<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 47

cgtagtaact tttattcgtg aaatgatttc att                               33
```